United States Patent
Koomson et al.

(10) Patent No.: US 10,561,319 B2
(45) Date of Patent: Feb. 18, 2020

(54) SYSTEM AND METHOD FOR MEASURING PHASE DELAY AND AMPLITUDE OF AN OPTICAL SIGNAL IN ANIMAL TISSUE

(71) Applicant: Tufts University, Medford, MA (US)

(72) Inventors: Valencia Koomson, Danvers, MA (US); Chirag Sthalekar, Burlington, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 16/229,387

(22) Filed: Dec. 21, 2018

(65) Prior Publication Data

US 2019/0110688 A1    Apr. 18, 2019

Related U.S. Application Data

(63) Continuation of application No. 15/116,444, filed as application No. PCT/US2015/014467 on Feb. 4, 2015, now Pat. No. 10,194,806.

(60) Provisional application No. 61/935,455, filed on Feb. 4, 2014.

(51) Int. Cl.
*A61B 5/05* (2006.01)
*A61B 5/00* (2006.01)
*A61B 5/1455* (2006.01)

(52) U.S. Cl.
CPC ........ *A61B 5/0075* (2013.01); *A61B 5/14552* (2013.01); *A61B 2560/0233* (2013.01); *A61B 2562/0238* (2013.01); *A61B 2562/0242* (2013.01); *A61B 2576/00* (2013.01)

(58) Field of Classification Search
CPC .......................... A61B 5/0075; A61B 5/14552
See application file for complete search history.

(56) References Cited

U.S. PATENT DOCUMENTS 6,246,892 B1    6/2001  Chance

FOREIGN PATENT DOCUMENTS

WO    WO 2009/128006 A1    10/2009

OTHER PUBLICATIONS

European Patent Office as the International Searching Authority, International Search Report and Written Opinion of the International Searching Authority, PCT/US2015/014467, dated May 6, 2015, 12 pages.
Sthalekar, et al., "A CMOS Sensor for Measurement of Cerebral Optical Coefficients Using Non-Invasive Frequency Domain Near Infrared Spectroscopy", IEEE Sensors Journal, vol. 13, No. 9, Sep. 1, 2013, pp. 3166-3174.

*Primary Examiner* — Michael J D Abreu
(74) *Attorney, Agent, or Firm* — Sunstein Kann Murphy & Timbers LLP

(57) ABSTRACT

A system and method, for measuring phase delay and amplitude of a near infrared signal emanating from tissue of an animal subject in response a near infrared signal input to such tissue, operate by processing a signal from an optical detector and a corresponding signal from an optical detector emulation circuit. In some aspects, the processed signals are fed into a phase delay detection system that provides an output thereof a digital measure of the phase delay of the received optical signal.

13 Claims, 4 Drawing Sheets

SYSTEM AND METHOD FOR MEASURING PHASE DELAY AND AMPLITUDE OF AN OPTICAL SIGNAL IN ANIMAL TISSUE

RELATED APPLICATION

This application claims priority to U.S. Application No. 61/935,455, entitled "Miniaturized Frequency Domain Near-Infrared Spectroscope" and filed Feb. 4, 2014, and U.S. application Ser. No. 15/116,444, entitled "System and Method for Measuring Phase Delay and Amplitude of a Near Infra-Red Signal in Animal Tissue" and filed Aug. 3, 2016, which is hereby incorporated by reference in its entirety.

GOVERNMENT SUPPORT

This invention was made with government support under grant DBI0953635 awarded by the National Science Foundation. The government has certain rights in the invention.

TECHNICAL FIELD

The present invention relates to optical tissue analysis systems, and more particularly to systems for measuring phase delay and amplitude of a near-infrared signal emanating from tissue of an animal subject in response to a near-infrared signal input to such tissue.

BACKGROUND ART

It is known in the prior art to measure phase delay and amplitude of a near-infrared signal emanating from tissue of an animal subject in response to a near-infrared signal input to such tissue. Such systems, however, tend to be bulky and to require significant power to operate.

SUMMARY OF THE EMBODIMENTS

In a first embodiment, the invention provides a system for measuring phase delay and amplitude, of a near infrared signal emanating from tissue of an animal subject, in response to a near infrared signal input to such tissue, wherein the phase delay and amplitude are the result of scattering and absorption by material in the tissue. The system includes a modulatable optical source providing an optical output in the near infrared frequency range, configured to be mounted to radiate into the tissue. The system also includes a local oscillator operative at a first frequency; and a reference oscillator operative at a second frequency and coupled to the modulatable optical source so that the optical output is modulated at the second frequency.

The system of this embodiment also includes a synchronization system, coupled to the local oscillator and to the reference oscillator, configured to synchronize the reference oscillator with the local oscillator in a manner that the difference between the second frequency and the first frequency is at least an order of magnitude smaller than the second. The system also includes an optical detector, configured to be mounted to receive an optical signal emanating from the tissue as a result of radiation by the optical source into the tissue and providing an electrical signal output as a result of receiving the optical signal.

Furthermore, the system of this first embodiment includes a signal processing unit having a plurality of channels, including a first channel coupled to the electrical signal output of the optical detector and a second channel coupled to an electrical signal output of an optical detector emulation circuit driven by the reference oscillator. In the first channel, a signal derived from the signal output of the optical detector is heterodyned with the local oscillator to produce a first intermediate frequency signal. In the second channel, a signal derived from the signal output of the optical detector emulation circuit is also heterodyned with the local oscillator to produce a second intermediate frequency signal.

The system of this first embodiment further includes a first zero crossing detector having an input coupled to the first intermediate frequency signal and providing a receiver channel square wave output, as well as a second zero crossing detector having an input coupled to the second intermediate frequency signal and providing a reference channel square wave output. The system further includes a time-to-digital converter coupled to the receiver channel square wave output and to the reference channel square wave output and providing at an output thereof a digital measure of the phase delay of the received optical signal. Moreover, the system includes a first amplitude detector coupled to the first intermediate frequency signal and having a first amplitude detection output; and a first analog-to-digital converter coupled to the first amplitude detection output so as to provide at an output thereof a digital measurement of the amplitude of the received optical signal.

In a further related embodiment, the synchronization system employs a phase-locked loop. Alternatively or in addition, the first amplitude detector includes a first peak detector. Also alternatively or in addition, the system includes a second amplitude detector coupled to the second intermediate frequency signal and a second analog-to-digital converter coupled to the second amplitude detection output so as to provide a digital output of the amplitude of a reference signal for calibration purposes. Alternatively or in addition, the second amplitude detector includes a second peak detector. Alternatively or in addition, the local oscillator, the reference oscillator, the synchronization system, and the signal processing unit are implemented as components in an integrated circuit. Optionally, the zero crossing detectors, the time-to-digital converter, each amplitude detector, and each analog-to-digital detector are also be implemented as components in the integrated circuit. Optionally, the system includes a wireless digital data transceiver coupled to the output of the time-to-digital converter and to the output of the analog-to-digital converter, so as to communicate wirelessly the digital measure of the phase delay of the received optical signal and the digital measurement of the amplitude of the received optical signal. Optionally, the system, excluding the optical source, consumes no more than 50 milliwatts of power. Optionally, the system occupies a volume less than 500 cc. Optionally, the system includes an adjustable compensation circuit to compensate for phase error in measurement of the phase delay of the received optical signal. Optionally, the adjustable compensation circuit includes an adjustable phase delay amplifier in series with the input to the second zero crossing detector.

Alternatively or in addition, the signal processing unit includes at least one additional channel coupled to a signal output of an additional optical detector, wherein a signal derived from the signal output of the additional optical detector is heterodyned with the local oscillator to produce an additional intermediate frequency signal; in this case, the system further includes:

an additional zero crossing detector having an input coupled to the additional intermediate frequency signal and providing an additional receiver channel square wave output;

an additional time-to-digital converter coupled to the additional receiver channel square wave output and to the reference channel square wave output and providing at an output a digital measure of the phase delay of the additional received optical signal;

an additional amplitude detector coupled to the additional intermediate frequency signal and having an additional amplitude detection output; and an additional analog-to-digital converter coupled to the first amplitude detection output so as to provide at an output a digital measurement of the amplitude of the additional received optical signal.

In another embodiment, the invention provides a method for measuring phase delay and amplitude, of a near infrared signal emanating from tissue of an animal subject in response to a near-infrared signal input to such tissue, wherein the phase delay and amplitude are the result of scattering and absorption by material in the tissue. The method of this embodiment includes:

providing an optical output, in the near infra-red frequency range, that radiates into the tissue;

running a local oscillator at a first frequency and a reference oscillator at a second frequency, wherein the second frequency is synchronized with the first frequency in a manner that the difference between the second frequency and the first frequency is at least an order of magnitude smaller than the second frequency;

using the reference oscillator to modulate the optical output;

receiving an optical signal emanating from the tissue as a result of radiation by the optical source into the tissue and providing an electrical signal output as a result of receiving the optical signal;

in a first signal processing channel, processing the received optical signal by heterodyning it with the local oscillator to produce a first intermediate frequency signal; and in a second signal processing channel, emulating a signal from an optical detector circuit that is modulated at the second frequency and also heterodyning the emulated signal with the local oscillator to produce a second intermediate frequency signal;

converting the first intermediate frequency signal into a receiver channel square wave;

converting the second intermediate frequency signal into a reference channel square wave;

feeding the receiver channel square wave and the reference channel square wave into a time-to-digital converter to provide at an output thereof a digital measure of the phase delay of the received optical signal;

detecting the amplitude of the first intermediate frequency signal and providing an analog amplitude detection output; and feeding the amplitude detection output into an analog-to-digital converter so as to provide at an output thereof a digital measurement of the amplitude of the received optical signal.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
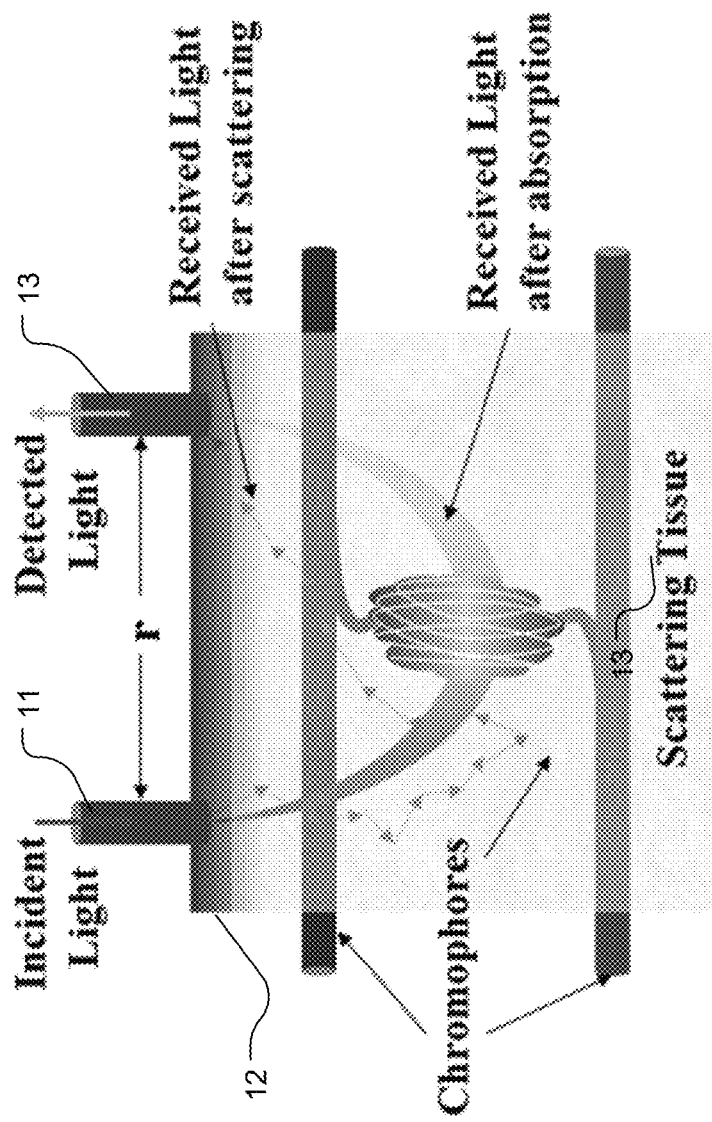
FIG. 1 depicts the absorption and scattering of infrared light incident upon animal tissue in a context pertinent to the present invention.

Near Infrared Spectroscopy (NIRS) is a non-invasive, nonionizing technique that uses light in the near infrared region (e.g., 600 nm-1000 nm) to measure the optical properties of tissue. FIG. 1 depicts the absorption and scattering of infrared light incident upon animal tissue in a context pertinent to the present invention. As depicted in FIG. 1, near-infrared light from source 11 may be projected onto animal tissue 12 and further detected by photodetector 13 on emerging from the tissue 12 after being partially absorbed and scattered by the tissue 12. Due to the low absorption of light by water in this region of the spectrum, several centimeters of tissue can be probed.

Various optical parameters (e.g., phase delay, amplitude, absorption and/or scattering coefficients) of the near-infrared light that has passed through animal tissue can be used to assess its structural and/or physiological properties. For example, concentrations of chromophores, such as oxy and de-oxy hemoglobin that have specific absorption spectra and may be used to indicate tissue health, may be derived from the absorption and scattering coefficients of tissue. Moreover, optical parameters may indicate the level of oxygenation in the tissue. Determining such properties of tissues has wide applicability in the fields of oncology, brain imaging (both adult and neonatal), neurological disorders, and mammography.

However, conventional spectroscopes are bulky and consume high amounts of power. In contrast, embodiments of the present invention may be fabricated on a chip, and consume low amounts of power while still achieving high-solution measurements of optical parameters. Thus, a spectroscope in accordance with an embodiment of the present invention may be a wearable, or otherwise portable, device readily used for point-of-care diagnosis. Moreover, such a spectroscope is conducive to monitoring tissue in subjects (e.g., patients in a hospital), for prolonged periods of time.

Figure 2:
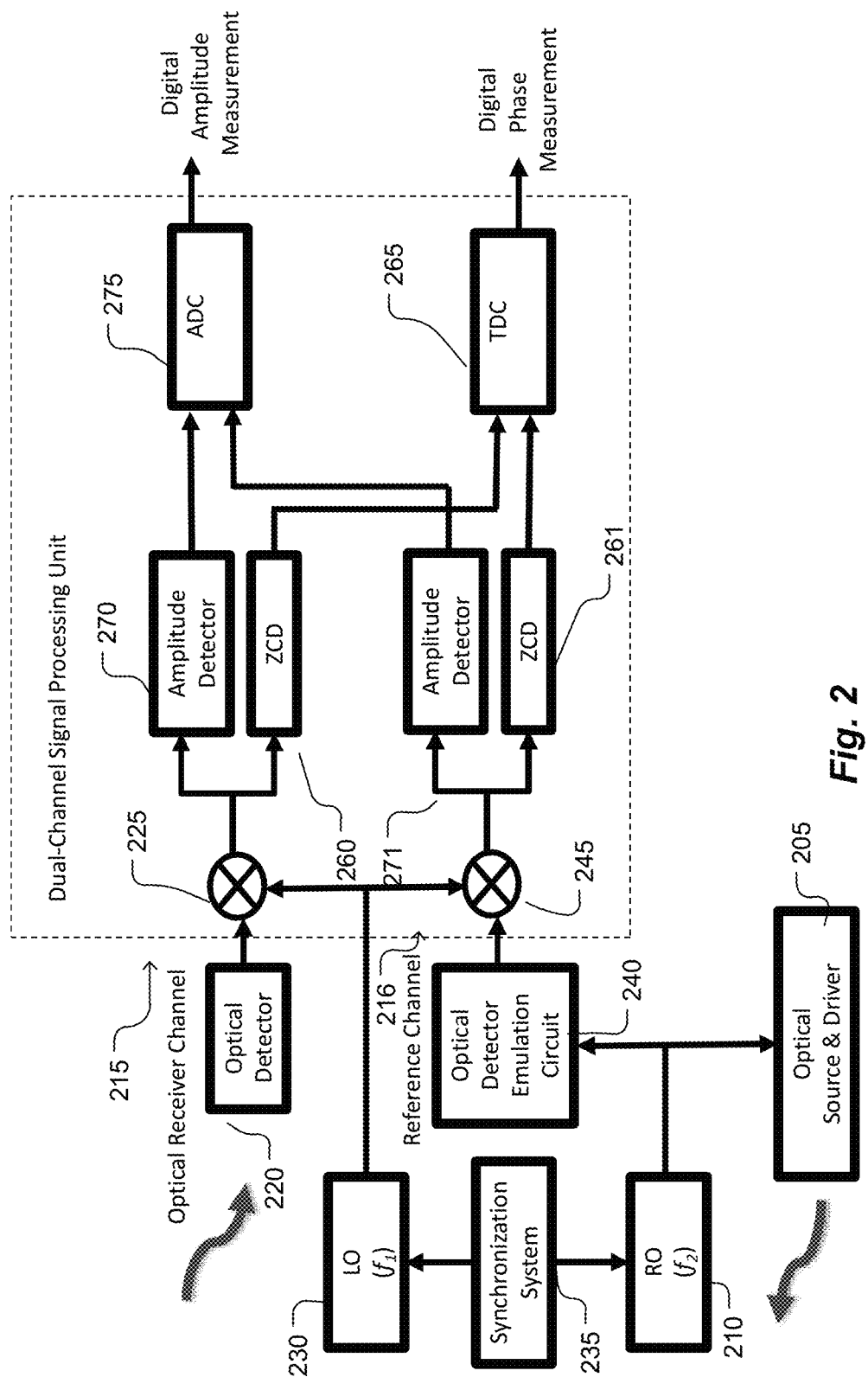
FIGS. 2 and 3 are block diagrams of exemplary systems in accordance with embodiments of the present invention, with a reference channel and a single optical receiver channel, that measure phase delay and amplitude in near infrared signals emanating from animal tissue that is exposed to a near-infrared light input.

A block diagram of an exemplary spectroscope 200 in accordance with an embodiment of the present invention is depicted in FIG. 2. The spectroscope 200 includes a reference channel and a single optical receiver channel, and the spectroscope 200 measures phase delay and amplitude in near infrared signals emanating from animal tissue that is exposed to a near-infrared light input.

The spectroscope 200 includes an optical source 205 configured to be mounted to radiate into a tissue. For example, the optical source 205 may be housed in a hand-held device which may be positioned against the surface of a subject's skin, proximate to a tissue to be examined. The optical source 205 emits light at a near infrared wavelength (e.g., 600 nm-1000 nm). A reference oscillator 210 coupled to the optical source 205 modulates the output from the optical source 205 at a high frequency, such as (80 MHz+40

KHz). By positioning the device against tissue, a user may direct the optical source 205 to radiate near infrared light modulated by the high frequency into a subject's skin.

The spectroscope 200 includes an optical receiver channel 215 that receives and analyzes the light after the light has been absorbed and scattered by the subject's tissue, as well as a reference channel 216. The receiver channel 215 includes an optical detector 220, such as an avalanche photodiode, that detects near infrared light emerging from the tissue. Due to prior modulation of the optical source 205 by the reference oscillator 210, the optical detector 220 receives and outputs an electrical puretone signal corresponding to the frequency of the reference oscillator (e.g., 80 MHz+40 KHz) and having a phase delay attenuation attributable to the travel of the received light through the tissue.

The mixer 225 heterodynes the signal from the optical detector 220 with the high frequency signal from local oscillator 230. A synchronization system 235 synchronizes the local oscillator 230 with the reference oscillator 210 to control their respective frequencies. In some embodiments, the synchronization system 235 synchronizes the local oscillator 230 with the reference oscillator 210 so that the difference between the frequencies of the oscillators is at least an order of magnitude smaller than the frequency of the local oscillator 230. For example, if the reference oscillator 210 provides a signal at 80 MHz+40 KHz, the local oscillator 230 may provide a signal at 80 MHz. Thus, the difference of 40 KHz is less than an order of magnitude smaller than 80 MHz.

Heterodyning the amplified signal with the signal from the local oscillator 230, the mixer 225 creates a signal with multiple components, including a component that is the difference between the frequencies. In our example, the received signal having a frequency of (80 MHz+40 KHz) heterodyned with 80 MHz signal from the local oscillator produces a difference signal of frequency by 40 KHz, which we term here "an intermediate frequency", which signal is used for measurement of the phase delay and amplitude of the received light from the tissue.

To determine the phase delay of the detected signal, the signal is compared against a reference signal, which is developed in the reference channel 216. The reference channel 2 includes optical detector emulation circuit 240, which is driven by reference oscillator 210. Similarly, the signal from the emulation circuit 240 is heterodyned in mixer 245 to produce a second intermediate frequency signal that serves as a reference for comparison with the output of the mixer 225.

At this point, both the optical receiver channel 215 and the reference channel 216 have produced signals modulated by a frequency that is the difference between the reference oscillator 210 and the local oscillator 230. A zero crossing detector (ZCD) 260 receives the signal in the optical receiver channel 215 and outputs a receiver channel square wave. Likewise, another zero crossing detector (ZCD) 261 receives the signal in the reference channel 216 and outputs a reference channel square wave. A time-to-digital converter (TDC) 265, coupled to the receiver channel square wave and to the reference channel square wave, produces at its output digital measure of the phase delay of the receiver channel square wave with respect to the reference.

Moreover, optical receiver channel 215 includes an amplitude detector 270 that receives the output of the mixer 225. Likewise, the reference channel 235 includes an amplitude detector 271 that receives the output of the mixer 245. The outputs of the amplitude detectors 270 and 271 are fed to the analog-to-digital converter (ADC) 275, provides at its output a digital measurement of the amplitude of the optical signal received by the optical detector 220. In this embodiment the output of amplitude detector 271 is used as a reference, although such is optional.

Figure 3:
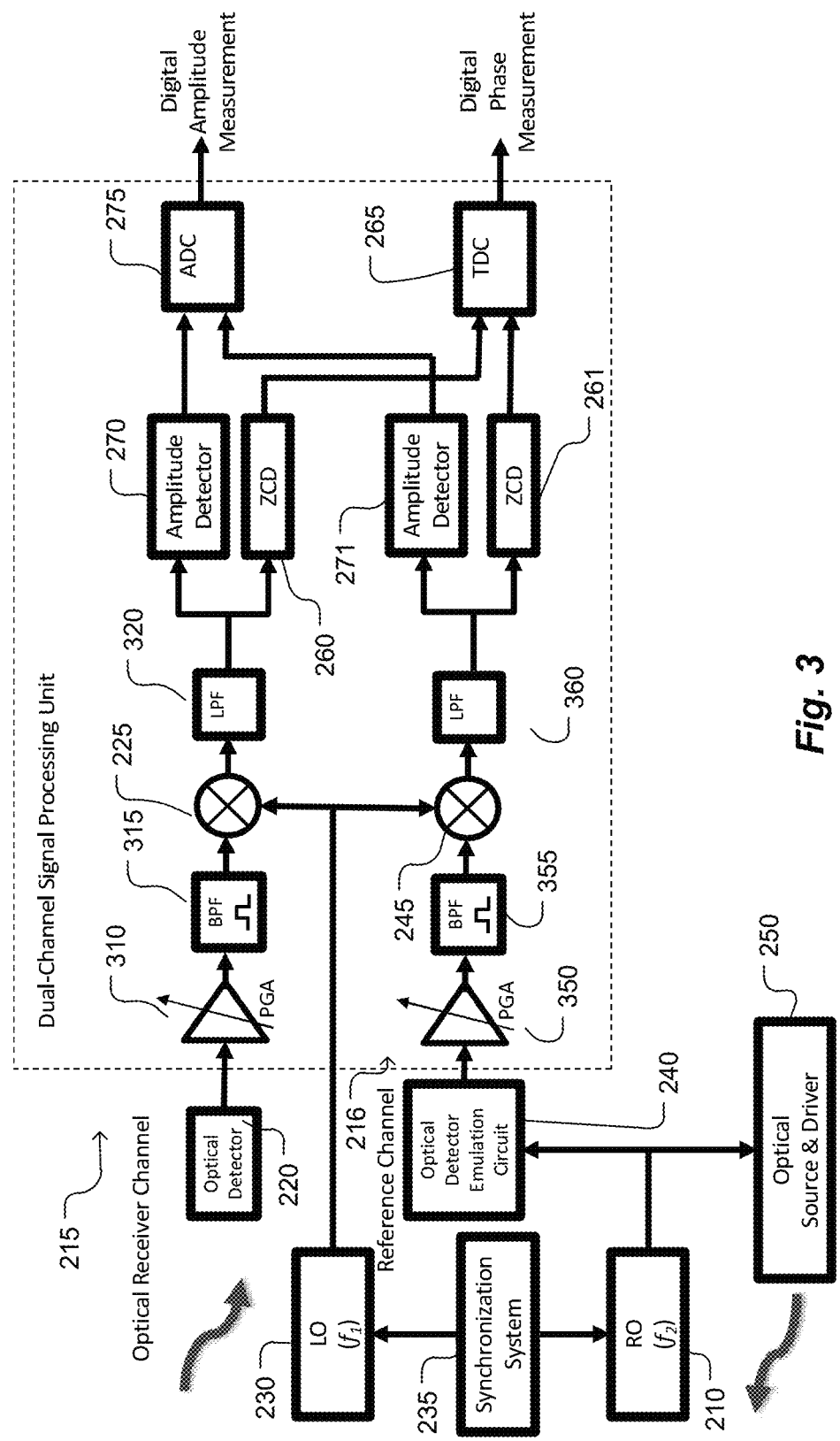

A more detailed block diagram of an exemplary spectroscope 300 in accordance with an embodiment of the present invention is depicted in FIG. 3. Like the spectroscope 200 in FIG. 2, the spectroscope 300 includes a reference channel and a single optical receiver channel, and the spectroscope 300 measures phase delay and amplitude in near infrared signals emanating from animal tissue that is exposed to a near-infrared light input.

The spectroscope 300 replicates the components of the spectroscope 200. However, in the spectroscope 300, the optical receiver channel 215 includes an amplifier 310, such as a programmable gain amplifier. Additionally, the optical receiver channel 215 includes a bandpass filter 315, which is typically centered on the frequency of the reference oscillator, to remove spurious components.

After heterodying the filtered received signal in mixer 225, the resulting signal is run through a low pass filter 320 to remove components above the intermediate frequency from the output of mixer 225. A parallel set of processing stages are followed in processing of the output of the optical detector emulation circuit 240 in the reference channel.

After the low pass filtering provided by low pass filters 320 and 360, the remainder of the processing is the same as in FIG. 2.

Figure 4:
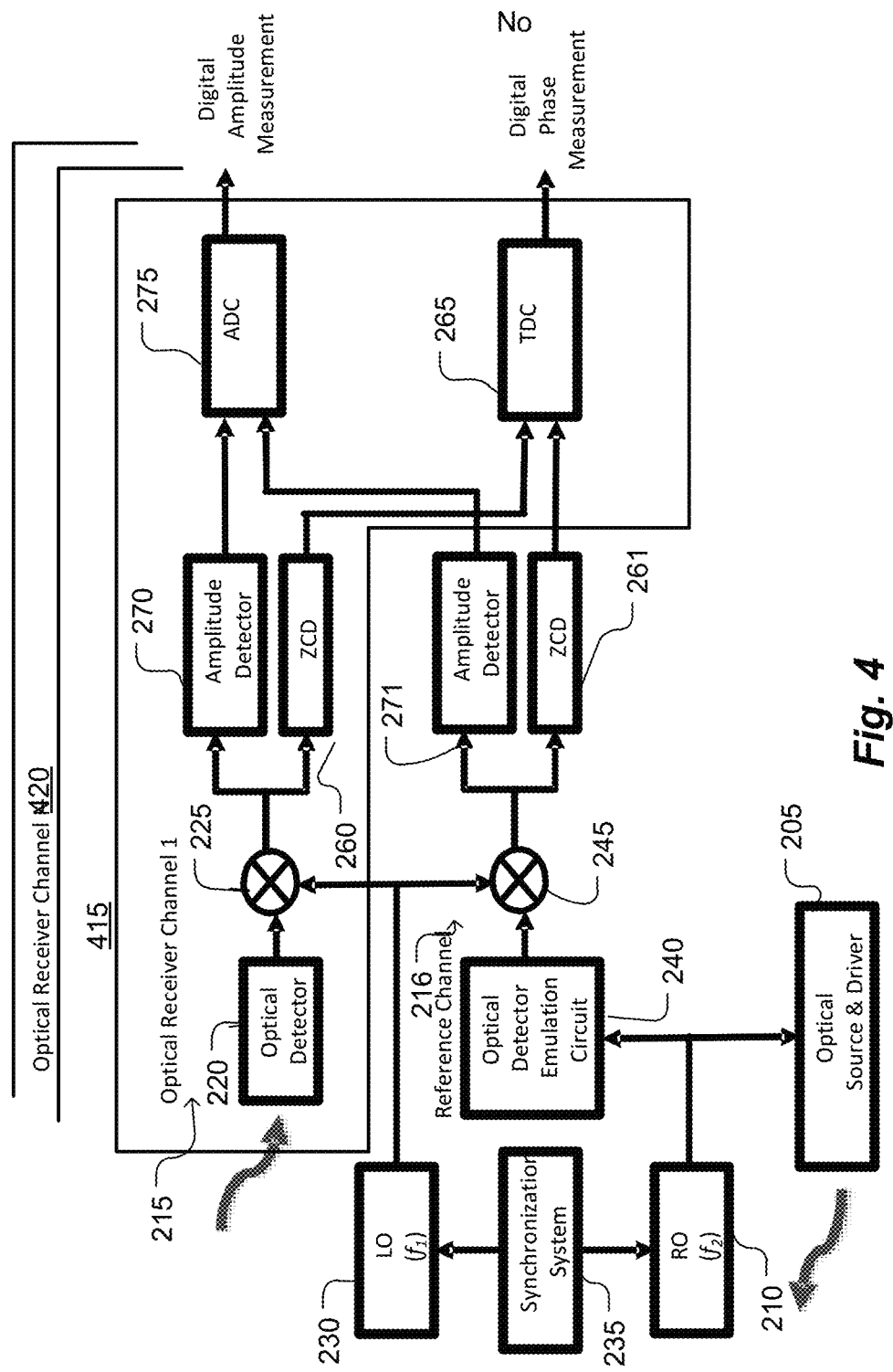
FIG. 4 is a block diagram of an exemplary system in accordance with an embodiment of the present invention, similar to that of FIG. 3, but with a plurality of optical receiver channels, that measure phase delay and amplitude in near infrared signals emanating from animal tissue that is similarly exposed to a near-infrared light input.

FIG. 4 is a block diagram of an exemplary spectroscope 400 in accordance with an embodiment of the present invention, similar to that of FIG. 2, but with a plurality of optical receiver channels 215, 415, 420, etc. that measure phase delay and amplitude of near infrared signals emanating from animal tissue that is similarly exposed to a near-infrared light input. In these embodiments, each optical receiver channel 215, 415, and 420 has a separate optical detector the output of which is separately processed and compared against the intermediate signal from the reference channel 216, as previously described in connection with FIG. 2.

In some embodiments, the spectroscopes are multi-distance (MD) devices. Each optical receiver channel uses the same near infrared wavelength of light, but the detectors are spaced apart from their corresponding optical sources, or a single optical source, by different distances. For example, the distance between any given detector and an optical source may be a multiple of a predetermined distance (e.g., 1×, 2×, 3×). The spectroscope may obtain the phase and amplitude measurements by the different detectors, and determine optical properties of the tissue based on these measurements.

In other embodiments, the spectroscopes are multi-frequency (MF) devices. In these devices, each detector is spaced from its corresponding optical source by the same distance, but at least two optical receiver channels use different modulating frequencies.

In any of the spectroscopes described herein, one or more components of the optical receiver channel 215 may be implemented as part of a complementary metal oxide semiconductor (CMOS) device. For example, a component may be fabricated in silicon, or silicon germanium (e.g., using SiGe heterojunction bipolar transistors). In some embodiments, as a result of the CMOS fabrication, the spectroscope draws less than 50 mW of power. The spectroscope may occupy a volume of less than 500 cc.

Any of the components described herein, such as local oscillator, the reference oscillator, the synchronization system, and the signal processing unit, may be implemented on an integrated circuit. In further examples, the zero crossing detectors, the time-to-digital converter, each amplitude detector, and each analog-to-digital detector may also be implemented as components in the integrated circuit. In some embodiments, all of the components are fabricated on the same circuit.

Numerous devices may be used for the optical source 205. The optical source 205 may include an array of near infrared lasers or light emitting diodes (LEDs). The array of near infrared optical sources may be selectively activated and deactivated by switches. Moreover, the optical source 205 may output light at more than one wavelength. For example, the optical source 205 may output light at 690 nm and 830 nm (e.g., at least one laser or LED emits light at 690 nm, and at least one other laser or LED emits light at 830 nm). In various embodiments, the optical source 205 may output light at wavelengths expressed by (690+n) nm and (690+m) nm, where n=(1, 2, . . . , 700) and m=(1, 2, . . . , 700). Different wavelengths may be used to monitor different properties of the tissue.

The reference oscillator 210 and the local oscillator 230 may output signals at frequencies between 50 MHz and 100 MHz. In some embodiments, the frequency of either oscillator may be expressed as 80 MHz+(40.0n) KHz, where n=(1, 2, . . . , 40). Alternatively, the frequency may be expressed as 80 MHz+(40.0n) KHz, where n=(1, 2, . . . , 40). The frequencies of the reference oscillator 210 and the local oscillator 230 may be selected such that the difference between the frequencies is less than an order of magnitude smaller than the frequency of the reference oscillator 210.

The synchronization system 235 that synchronizes the local oscillator 230 with the reference oscillator 210 may be a phase locked loop, an open loop, or a feed forward control.

In various embodiments, the optical detectors 220 described herein may be avalanche photodiodes (APD). In contrast to photomultiplier tubes, which are highly sensitive to light, the avalanche photodiodes require comparatively little energy to operate. For example, the avalanche photodiodes require much smaller biasing voltages than the photomultiplier tubes. As a result, the spectroscopes with avalanche photodiodes do not require high voltage power supplies. In some embodiments, the detector of an avalanche photodiode may have a cross section with a surface area on the order of 1.7 mm$^2$. In some embodiments, the detector of an avalanche photodiode may have a cross section with a surface area of at least 7 mm$^2$. In various embodiments, the surface area may be expressed by (2+n(0.25)) mm$^2$, for n=0 to 50, in steps of 1.

The amplifier 310 or 350 may be a trans-impedance amplifier coupled to an automatic gain control. The automatic gain control may receive the output of the trans-impedance amplifier, and adjust the gain of the amplifier in response. The amplitude detector 270 or 271 may be a peak detector, such as a peak envelope detector. The peak detector may generate a DC voltage corresponding to the peak of the received signal. In other embodiments, the amplitude detector 270 or 271 may output the root-mean-squared (RMS) value of the amplitude of the input signal.

In some embodiments, the spectroscope includes a wireless digital data transceiver (not shown). The wireless transceiver may be coupled to the output of the time-to-digital converter (TDC) 265 and the output of the analog-to-digital converter (ADC) 275. The wireless transceiver may transmit, via an antenna, information about the near infrared light received by the detector to another device. For example, the wireless transceiver may transmit information about the phase delay or amplitude to a data storage device. As the spectroscope continues to obtain and transmit information about the tissue, the data storage device may store the information to build a history of the tissue's properties.

Further, the data storage device may be a computer, a smart phone, or any other portable device that provides local data storage and further transmission of that stored data. This is particularly useful in the case of a portable apparatus since a patient would find it difficult to carry out normal activities while tethered to a data storage device.

The spectroscope may be configured to store the data on a removable memory element. For example, the spectroscope may receive a memory card or a memory stick. Instead of transmitting the data to a remote device, the spectroscope may store the data locally. Thus, users may remove the memory card to load the data onto another computing system, and replace the used card with a new one.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system for measuring phase delay and amplitude, of an optical signal emanating from tissue of an animal subject, in response to an optical signal input to such tissue, wherein the phase delay and amplitude are the result of scattering and absorption by material in the tissue, the system comprising:
   a modulatable optical source, configured to be mounted to radiate into the tissue;
   a local oscillator operative at a first frequency;
   a reference oscillator, operative at a second frequency, and coupled to the modulatable optical source so that the optical output is modulated at the second frequency;
   a synchronization system, coupled to the local oscillator and to the reference oscillator, configured to synchronize the reference oscillator with the local oscillator in a manner that the difference between the second frequency and the first frequency is fixed;
   an optical detector, configured to be mounted to receive an optical signal emanating from the tissue as a result of radiation by the optical source into the tissue and providing an electrical signal output as a result of receiving the optical signal;
   a signal processing unit having a plurality of channels, including a first channel coupled to the electrical signal output of the optical detector and a second channel coupled to an electrical signal output of an optical detector emulation circuit driven by the reference oscillator, wherein:
     in the first channel a signal derived from the signal output of the optical detector is heterodyned with the local oscillator to produce a first intermediate frequency signal; and
     in the second channel a signal derived from the signal output of the optical detector emulation circuit is also heterodyned with the local oscillator to produce a second intermediate frequency signal;
   a phase delay detection system coupled to the first and second channels providing an output that is a measure of phase difference between the first and second intermediate frequency signals;
   a first amplitude detector coupled to the first intermediate frequency signal and having a first amplitude detection output; and a first analog-to-digital converter coupled to the first amplitude detection output so as to provide at an output thereof a digital measurement of the amplitude of the received optical signal.

2. A system according to claim 1, wherein the synchronization system employs a phase-locked loop.

3. A system according to claim 1, wherein the first amplitude detector includes a first peak detector.

4. A system according to claim 1, further comprising a second amplitude detector coupled to the second intermediate frequency signal and a second analog-to-digital converter coupled to the second amplitude detection output so as to provide a digital output of the amplitude of a reference signal for calibration purposes.

5. A system according to claim 1, further comprising a second amplitude detector with a second peak detector.

6. A system according to claim 1, wherein the local oscillator, the reference oscillator, the synchronization system, and the signal processing unit are implemented as components in an integrated circuit.

7. A system according to claim 1, further comprising a wireless digital data transceiver coupled to the output of the phase delay detection system and to the output of the first analog-to-digital converter, so as to communicate wirelessly the digital measure of the phase delay of the received optical signal and the digital measurement of the amplitude of the received optical signal.

8. A system according to claim 1, wherein the system, excluding the optical source, consumes no more than 50 milliwatts of power.

9. A system according to claim 1, wherein the system occupies a volume less than 200 cc, including the optical source and the optical detector.

10. A system according to claim 1, wherein the system occupies a volume less than 1 cc, including the optical source and the optical detector.

11. A system according to claim 1, further comprising an adjustable compensation circuit to compensate for phase error in measurement of the phase delay of the received optical signal.

12. A system according to claim 1, wherein the adjustable compensation circuit includes an adjustable phase delay amplifier.

13. A system according to claim 1, wherein the signal processing unit includes at least one additional channel coupled to a signal output of an additional optical detector, wherein a signal derived from the signal output of the additional optical detector is heterodyned with the local oscillator to produce an additional intermediate frequency signal, the system further comprising:

an additional phase delay detection system having an input coupled to the additional intermediate frequency signal and providing an additional output that is a measure of phase difference between the additional and second intermediate frequency signals;

an additional amplitude detector coupled to the additional intermediate frequency signal and having an additional amplitude detection output; and an additional analog-to-digital converter coupled to the additional amplitude detection output so as to provide at an output a digital measurement of the amplitude of the additional received optical signal.

* * * * *